United States Patent [19]

Exton

[11] 4,063,282
[45] Dec. 13, 1977

[54] TV FATIGUE CRACK MONITORING SYSTEM

[75] Inventor: Reginald J. Exton, Williamsburg, Va.

[73] Assignee: The United States of America as represented by the Administrator of the National Aeronautics and Space Administration, Washington, D.C.

[21] Appl. No.: 707,125

[22] Filed: July 20, 1976

[51] Int. Cl.² .............................................. H04N 7/18
[52] U.S. Cl. .................................................... 358/106
[58] Field of Search ................. 358/106, 107, 100, 93, 358/108

[56] References Cited

U.S. PATENT DOCUMENTS

| | | | |
|---|---|---|---|
| 2,164,125 | 6/1939 | Sokoloff | 358/106 |
| 2,798,605 | 7/1957 | Richards | 358/93 |
| 3,256,386 | 6/1966 | Morchand | 358/93 |

Primary Examiner—Richard Murray
Attorney, Agent, or Firm—Howard J. Osborn; William H. King; John R. Manning

[57] ABSTRACT

An apparatus is disclosed for monitoring the development and growth of fatigue cracks in a test specimen subjected to a pulsating tensile load. A plurality of television cameras photograph a test specimen which is illuminated at the point of maximum tensile stress. The television cameras have a modified vidicon tube which has an increased persistence time thereby eliminating flicker in the displayed images.

7 Claims, 2 Drawing Figures

U.S. Patent  Dec. 13, 1977  4,063,282
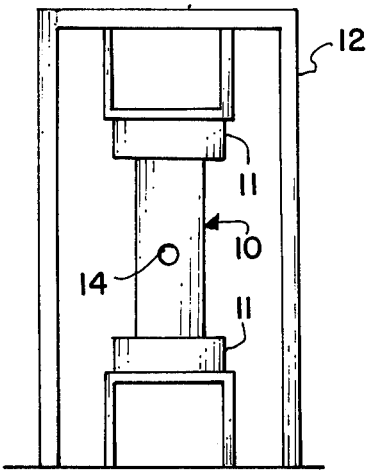
FIG. 1
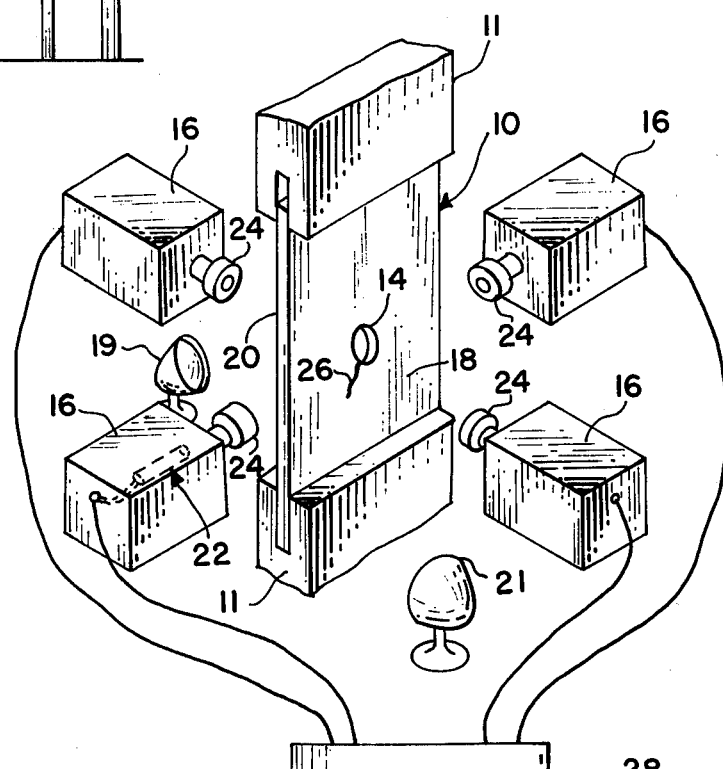
FIG. 2
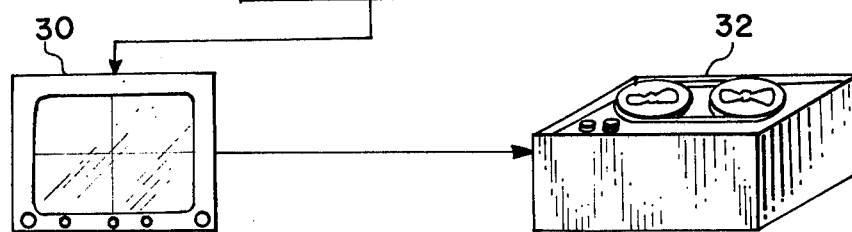

TV FATIGUE CRACK MONITORING SYSTEM

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention

This invention generally relates to apparatus using television cameras to inspect the surface of an object, and more particularly to apparatus using television cameras to detect the initiation and growth of fatigue cracks in a test specimen. Thus the fatigue failure of a test specimen can be observed and recorded for study without the need for an operator to be present throughout the duration of the tests.

2. Description of the Prior Art

The use of television cameras to inspect an object whose surface changes with respect to time or which is moving rapidly are well known. U.S. Pat. No. 3,111,555, for example, teaches an apparatus which uses a television camera to permit visual inspection of the surface of a rapidly moving metal strip. Similarly, U.S. Pat. No. 3,176,306 uses a television camera to detect imperfections on the surface of a rapidly moving tin sheet. In other applications, a television camera has been used in apparatus designed for analyzing sprays as in U.S. Pat. No. 3,275,744; counting and measuring small particles as in U.S. Pat. No. 3,390,229; and for determining the dimensions of a rapidly moving object as in U.S. Pat. No. 3,666,885. Typical of other devices using a television camera are U.S. Pat. Nos. 3,294,002 and 3,679,823.

While these earlier developments use a television camera to view a moving object, they lack the aspects of the present invention wherein a plurality of television cameras are used to record the initiation and growth of a fatigue crack in a test specimen. In addition, the prior art uses of a television camera are limited to those instances in which the sequence of lighting and photographing the object can be timed to coincide with the persistence time of the existing vidicon tube of the camera.

It is therefore an object of the present invention to provide an apparatus for detecting surface cracks in fatigue specimens.

The further object of the present invention is an apparatus for making a visual recording of the initiation and propagation of fatigue cracks.

These and other objects of the invention will be readily apparent when considered in reference to the description and claims and taken in connection with the attached drawings to which they relate.

SUMMARY OF THE INVENTION

In the present invention, the test specimen is subjected to a pulsating tensile load. A plurality of television cameras are positioned around the spcimen so as to photograph the surfaces of the specimen which are periodically lighted by strobe lights. The strobe lights are synchronized so that the specimen is lighted when it is subjected to the maximum tensile load thereby making detection of fatigue cracks easier.

The television cameras have a modified vidicon tube which increases the persistence time of the cameras. The persistence time is the time required for the video signal to fall to one-half of its original value. Unmodified vidicon tubes have a persistence time which is much shorter than the time between load cycles of the test specimen. This condition causes a flickering on the television screen which is eliminated when the persistence time of the vidicon tube is increased.

A special effects generator receives the pictures from each camera and displays them simultaneously on a television monitor. At the same time, the television picture is recorded for later playback on a video tape recorder.

DESCRIPTION OF THE DRAWINGS

FIG. 1 is the front view of a specimen on a testing machine;

FIG. 2 is a perspective view of the present invention.

DESCRIPTION OF THE PREFERRED EMBODIMENT

Referring now to the drawings, there is shown a preferred embodiment of the invention as it would be used to detect fatigue cracks in a laboratory specimen subjected to a pulsating load.

As best seen in FIG. 1, specimen 10 is placed in the grips 11 of the testing machine 12 which is capable of applying a pulsating tensile load. The specimen 10 may be of any shape or of any material and, further, may be either solid or perforated. As shown in FIG. 1, specimen 10 has a single hole 14 drilled therethrough.

Referring now to FIG. 2, it can be seen that cameras 16 are positioned around the specimen so as to photograph the front and back surfaces 18 and 20, respectively, of specimen 10. In the preferred embodiment, four cameras 16 are used; however, a lesser or greater number may be used if necessary. Many manufacturers produce cameras suitable for use in the present apparatus such as Cohu Corporation's camera, Model 2810, which is in the preferred embodiment. Specimen 10 is illuminated by strobe lamps 19 and 21, which have a one micro-second duration and which are timed to illuminate specimen 10 when testing machine 12 (Not shown in FIG. 2) is applying the maximum tensile load to specimen 10. Strobe lamps 19 and 29 are positioned so that very little light is reflected from surfaces 18 and 20 toward lens 24 of cameras 16. As fatigue crack 26 develops and grows, it scatters light toward lens 24 causing crack 26 to appear white against a black background in the photographs.

Cameras 16 have a vidicon tube 22 which has a persistence time selected to eliminate flicker. A testing machine operating at 1200 cycles per minute (20 Hertz) would generate one pulse of strobe lamps 19 and 21 every 50 milliseconds. Since a standard vidicon tube has a persistence time of only 15 milliseconds, the result is one bright field in which the flash occurs followed by several fields in which there is no illumination. The resulting flicker renders the pictures unsuitable for data analysis and makes viewing difficult.

By increasing the persistence time of the vidicon tube 22, flicker is eliminated. In the preferred embodiment, a vidicon tube 22 having a persistence time of 250 milliseconds was used. Such vidicon tubes 22 are manufactured by Teltron Incorporated of Douglasville, Pennsylvania.

Cameras 16 are connected to a special effects generator 28 which permits the pictures from each camera to be displayed simultaneously on television monitor 30. Since four cameras were used in the preferred embodiment, a quad split generator model 938 manufactured by Grass Valley Group, Incorporated of Grass Valley, California was used.

Video tape recorder 32 is used to record the pictures taken by cameras 16. Although any suitable recorder may be used, model 960 manufactured by International Video Corporation was used in the preferred embodiment.

It will be understood that the foregoing description is of the preferred embodiment of the invention and is therefore merely representative. Obviously, there are many variations and modifications of the present invention in light of the above teachings. It is therefore to be understood that within the scope of the appended claims the invention may be practiced otherwise than as specifically described.

What is claimed as new and described to be secured by Letters Patent of the United States is:

1. A fatigue crack monitoring apparatus comprising a specimen which is subjected to a pulsating tensile load which varies from a maximum to a minimum; a strobe light means for illuminating said specimen; a video means for taking television pictures of said specimen; a display means for displaying said television pictures; and a recording means for recording said television pictures.

2. The apparatus of claim 1 wherein said strobe light means comprises a plurality of strobe lights which are directed toward said specimen and which illuminates said specimen only when the maximum tensile load is applied to said specimen.

3. The apparatus of claim 1 wherein said video means comprises a plurality of television cameras positioned to photograph said specimen.

4. The apparatus of claim 3 wherein said television cameras are equipped with a vidicon tube having a persistence time which is longer than the time required from the pulsating tensile load to move through one cycle.

5. The apparatus of claim 3 wherein said plurality of strobe lights are positioned relative to said specimen and said cameras such that very little light from said strobe lights are reflected toward the lens of said television cameras whereby whenever a fatigue crack develops and grows the crack scatters light toward the lens of said cameras causing the crack to appear white against a black background in the photographs produced by said cameras.

6. The apparatus of claim 3 wherein said display means comprises a special effects generator and a television monitor; said special effects generator being capable of allocating a portion of said monitor for the simultaneous display of the pictures from said plurality of cameras.

7. The apparatus of claim 3 wherein said recording means is a video tape recorder.

* * * * *